United States Patent [19]

Burgess et al.

[11] 4,396,584

[45] Aug. 2, 1983

[54] BLOOD OXYGENATOR

[75] Inventors: Mike Burgess, P.O. Box 572, Avalon, Calif. 90704; Cyril I. Hall, Avalon, Calif.

[73] Assignee: Mike Burgess, Avalon, Calif.

[21] Appl. No.: 268,757

[22] Filed: Jun. 1, 1981

[51] Int. Cl.³ .............................................. A61M 1/03
[52] U.S. Cl. .............................. 422/310; 128/DIG. 3; 261/DIG. 28; 422/46; 422/47
[58] Field of Search ........................... 422/46, 47, 310; 128/DIG. 3; 261/DIG. 28

[56] References Cited

U.S. PATENT DOCUMENTS

| 3,578,411 | 5/1971 | Bentley et al. | 422/46 X |
|---|---|---|---|
| 3,769,162 | 10/1973 | Brum et al. | 422/46 X |
| 3,807,958 | 4/1974 | Brumfield et al. | 422/46 |
| 4,138,464 | 2/1979 | Lawin | 422/46 |
| 4,180,896 | 1/1980 | Reed et al. | 422/46 X |
| 4,203,945 | 5/1980 | De Wall | 422/46 X |
| 4,261,951 | 4/1981 | Milev | 422/46 |
| 4,268,476 | 5/1981 | Raible | 422/46 |
| 4,282,180 | 8/1981 | Raible | 422/46 |
| 4,297,318 | 10/1981 | Raible | 422/46 |

FOREIGN PATENT DOCUMENTS 2040175 8/1980 United Kingdom ....... 261/DIG. 28

OTHER PUBLICATIONS

"D-750" Thermoflow Bubble Oxygenator, Delta Medical Industries, Costa Mesa, Calif.
"The Elliptical Model H-1500 Hybrid Disposable Oxygenator", Texas Medical Products, Inc.
"Shiley 100A Oxygenator", photo from The Journal of Extra-Corporeal Technology-copyright, Amsect, 1979.
Spiraflo BOS-10, Bentley Laboratories, Inc., Irvine, Calif.

Primary Examiner—Barry S. Richman
Attorney, Agent, or Firm—Charles H. Thomas

[57] ABSTRACT

A blood oxygenator is equipped with a sparger having a passageway formed by two vertically aligned fluid impervious cones, one upright and one inverted, between the bases of which a porous disc is positioned. An oxygen inlet communicates with the porous disc to radially inject oxygen into the passageway from the periphery of the porous disc. The blood is transformed from a liquid to a foam as it rises in the passageway. At the outlet of the sparger an oxygenation chamber includes a serpentine cascade which prolongs contact between the blood and bubbles of gas containing oxygen. The outlet of the cascade empties into a reservoir which has a concave foam filter therein defining a defoaming chamber and a screen having uniform interstices surrounding the foam filter to form a bubble point barrier. The screen prevents undissolved gaseous emboli in the blood from passing from the defoaming chamber toward the arterial outlet of the reservoir.

8 Claims, 8 Drawing Figures

BLOOD OXYGENATOR

BACKGROUND OF THE INVENTION

1. Field of the Invention

The present invention relates to blood oxygenating devices which are used during cardiac and lung surgery to remove dissolved carbon dioxide and introduce dissolved oxygen into the blood of an anesthetized patient undergoing surgery.

2. Description of the Prior Art

The advances of medical technology in recent years now allow surgeons to perform intricate cardiac and lung surgery not previously possible. Surgery can be performed in which the heart and lungs of a patient are temporarily disabled and do not perform their normal vital functions of removing carbon dioxide and providing oxygen to the patient's blood and pumping the blood through the body of the patient. During the interval that the heart and lungs do not perform these vital functions, some artificial means of providing oxygen to the blood of the patient and circulating the blood through the patient's body must be provided.

A number of conventional blood oxygenating devices are presently commercially available. Originally, blood oxygenators typically provided a heat exchanger in the arterial reservoir of blood. The arterial reservoir in a blood oxygenator contains the blood which has been reoxygenated and is ready for return to the patient's body. Typical among such blood oxygenators are the Bentley Q-100, manufactured by Bentley Laboratories, Irvine, Calif., and the Optiflo I oxygenator manufactured by Cobe Laboratories, Denver, Colo. The purpose of the heat exchanger is to maintain the blood at the body temperature of the patient as it is returned to the patient. However, certain technical difficulties arose with the placement of a heat exchanger in oxygenated blood. Specifically, the problem foreseen was that of generation of gaseous emboli caused by heating an oxygen rich solution such as blood, or more specifically plasma with oxygen and other gases dissolved therein. Such gaseous emboli could be quite dangerous to a patient if they are introduced into the arterial line returning blood to the patient. The likelihood of introduction of gaseous emboli into the patient is enhanced if the heat exchanger is placed in the arterial reservoir of blood to be returned to the patient.

Accordingly, blood oxygenators were developed in which the heat exchanger was moved to the venous side of the blood oxygenator to reduce the hazard of potential emboli and to increase the heat exchange efficiency. Commercial blood oxygenators of this type include the Shiley 100 A Oxygenator, manufactured by Shiley Laboratories of Irvine, Calif., the Bentley Spiraflo BOS-10 Blood Oxygenator manufactured by Bentley Laboratories, Inc., of Irvine, Calif., the Optiflo II Blood oxygenator and the D-750 Thermoflow Oxygenator, manufactured by Delta Medical Industries of Costa Mesa, Calif. However, by moving the heat exchanger to the venous or inlet side of the blood oxygenator, a degree of temperature control is lost, since the reoxygenated blood may remain in an arterial reservoir for a variable period of time prior to return to the patient.

Another problem which has existed in blood oxygenators is the limited efficiency of oxygen transfer which has heretofore been achieved. Oxygen transfer is effectuated by transforming the liquid blood from the venous inlet into a foam. This is achieved by the introduction of gaseous oxygen into the blood. As oxygen bubbles pass through the blood the blood is converted from a liquid to a foam. However, with conventional spargers which introduce oxygen into the blood, only a relatively slow rate of oxygen transfer has heretofore been achieved. As a consequence, a greater volume of blood is necessary for use during surgery since the rate of reoxygenation of blood is relatively slow.

SUMMARY OF THE INVENTION

One object of the present invention is to provide a blood oxygenator with a sparger which significantly increases the rate at which a given volume of blood is converted from a liquid to a foam. This object is achieved with the unique sparger structure which employs in a sparger housing two vertically aligned, fluid impervious cones, positioned base to base one upright and one inverted, with a porous disc sandwiched therebetween. An oxygen inlet tube is in communication with the center of the porous disc. Oxygen is introduced into the porous disc and flows outwardly to introduce oxygen radially into the annular passageway which is formed between the cones and the disc on one side and the housing on the other.

The passageway follows the contour of the two cones. The passageway is of a uniform width throughout, but because the cross-sectional diameter of the cone increases from the venous inlet to the porous disc, the overall cross-sectional area of the passageway likewise increases from the inlet to the porous disc. Where the oxygen is introduced at the periphery of the disc, the passageway has the greatest cross-sectional area. Once the blood is transformed to a foam, the foam bubbles tend to rise upwardly along the conical surface of the upright cone. The cross-sectional area of the passageway diminishes with distance from the porous disc until it reaches its smallest cross-sectional area at the apex of the upright cone which is at the sparger outlet. This reduction in cross-sectional area into which the foam bubbles rise increases pressure on the foam bubbles slightly, thereby further inducing oxygenation of the blood.

The width of the passageway in the sparger is fairly critical. The passageway width must be between one thirty-second and three-eighths of an inch, and preferably is three thirty seconds of an inch. With appropriate passageway dimensions such as these, the foam bubbles formed in the blood tend to form at a diameter just about equal to the passageway width. This prevents the blood from flowing past the gas bubbles in the passageway toward the sparger outlet. Instead, the blood is forced into contact with the gas bubbles.

A further feature of the size of the sparger is that the cross-sectional area at the sparger outlet should be about one-half inch or more, and is equal to or greater than the area at the venous inlet to the sparger. With a sparger outlet greater in cross-sectional area than the sparger inlet, a back pressure is avoided so that upward flow of the foam to the outlet of the sparger can be maintained. Preferably, the inclination of the sides of the cone from the vertical is about 30 degrees. A significant degree of convergence at the cone apex is thereby achieved, but the surface of the cone is inclined steeply enough so that the foam bubbles rise freely.

A further object of the invention is to provide a sparger having the shortest possible height, but which still effectuates complete conversion of the blood from a liquid to a foam. This reduces the total volume of blood required in the blood oxygenator.

Another object of the invention is to increase the residence time of contact between the oxygen and the blood once the blood is discharged from the sparger outlet. This is achieved by providing a serpentine cascade in which the blood discharged from the sparger outlet flows back and forth down inclined ramps, partly as a liquid but primarily as a foam, to the oxygenating chamber outlet. In this fashion, the time of contact between oxygen and blood in a foam state is increased within a relatively small volume.

A further object of the invention is to provide a blood oxygenator with an arterial reservoir within which a heat exchanger is located. Within the arterial reservoir of the invention there is a concave foam filter which defines a defoaming chamber. A screen having uniform interstices therein surrounds the foam filter to form a bubble point barrier that prevents undissolved gaseous emboli in blood passing from the defoaming chamber to the arterial outlet. By constructing the screen with uniform interstices, preferably as a mesh having mesh openings between about 50 microns and 150 microns absolute, a barrier to bubbles is achieved. That is, bubbles contacting the screen, wet with arterialized blood, cannot pass through the interstices because of the surface tension of the liquid blood on the screen. As a result such bubbles in the defoaming chamber rise upwardly ultimately to the surface of the blood in the reservoir. With the bubble screen of the invention surrounding the defoaming chamber, it is practical to locate a heat exchanger in the defoaming chamber without the danger to the patient of gaseous emboli, which might be generated by contact between the arterialized blood and the heat exchanger coils.

In one embodiment of the invention the heat exchanger coils are helical coils formed into elongated upright loops that extend from the bottom of the defoaming chamber to above the height of the foam filter. The blood as it emanates from the oxygenating chamber runs in sheets down the surfaces of the upright loops of the helical coils so that heat transfer is effectuated to the arterialized blood.

Preferably, a flow guide is located between the upper extremities of the upright heat exchanger loops and the outlet of the oxygenation chamber. The flow guide directs the flow of blood from the oxygenation chamber onto the upper extremities of the heat exchanger coils and into the defoaming chamber. The flow guide prevents blood leaving the oxygenation chamber from falling into the reservoir outside of the defoaming chamber.

A further object of the invention is to provide the reservoir with a structure which prevents vortexing of the arterialized blood as it is withdrawn for return to the patient. Vortexing could well result in air being drawn into the arterial outlet. Such air in the blood being returned to the patient would form gaseous emboli which would be extremely hazardous to the patient. By employing an arrangement of baffles within the lower portion of the reservoir and by positioning a vortex inhibiting structure in the arterial outlet below the reservoir, entrainment of air in blood returned to the patient can be avoided.

The invention may be described with greater clarity and particularity by reference to the accompanying drawings.

DESCRIPTION OF THE DRAWINGS

FIG. 3 is a sectional detail taken along the lines 3—3 of FIG. 2.

FIG. 5 is a sectional plan view taken along the lines 5—5 of FIG. 2.

FIG. 6 is a sectional plan view taken along the lines 6—6 of FIG. 2.

FIG. 7 is a perspective view of an alternative heat exchange coil arrangement.

FIG. 8 is a sectional detail taken along the lines 8—8 of FIG. 7.

DESCRIPTION OF THE EMBODIMENTS

Figures 2, 4:
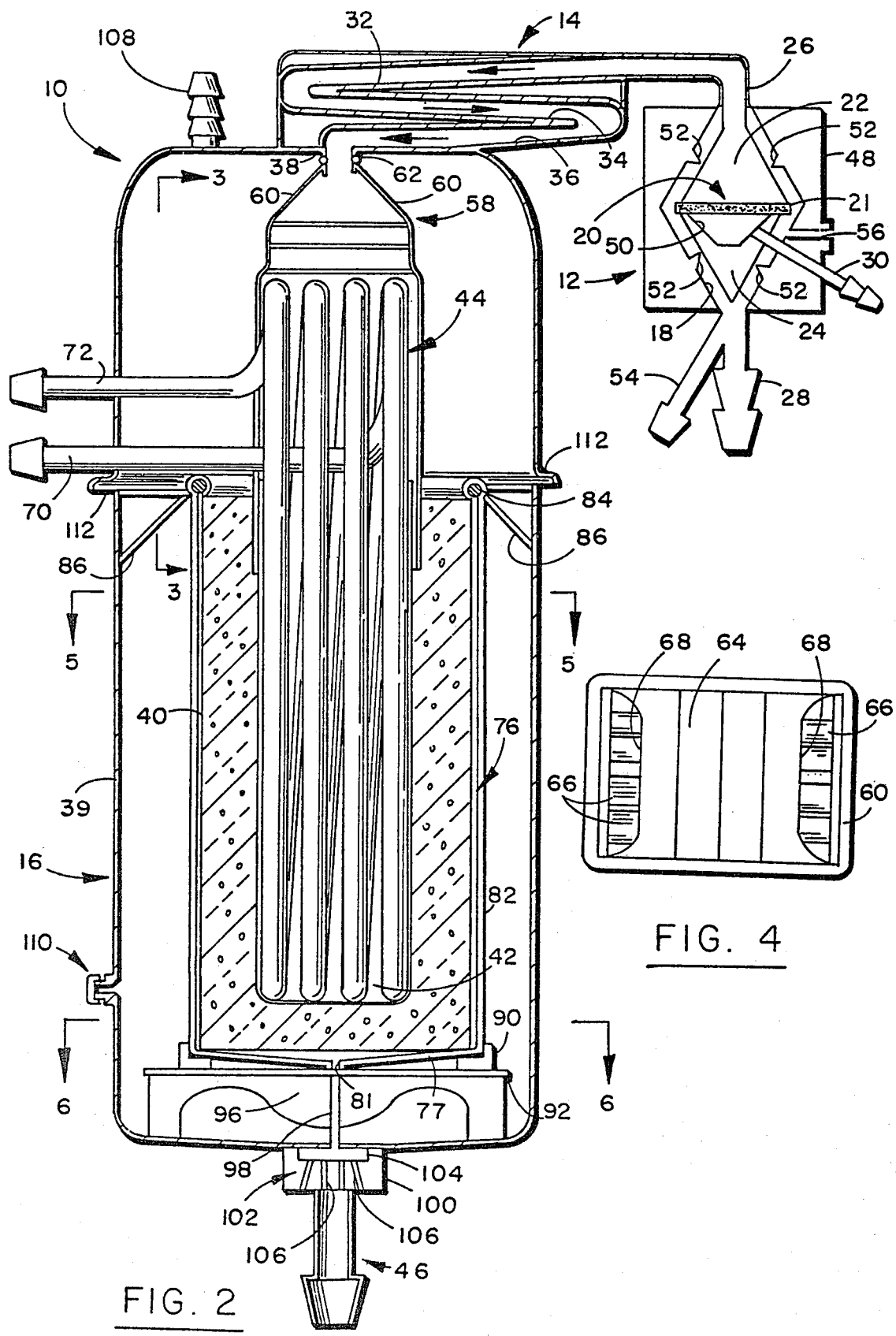
FIG. 2 is a side elevational view of the blood oxygenator of FIG. 1.
FIG. 4 is a sectional plan detail taken along the lines 4—4 of FIG. 3.

With reference to FIG. 2 a blood oxygenator 10 is provided according to the invention and includes a sparger 12, an oxygenation chamber 14 and a reservoir 16. The sparger 12 has defined therein an annular passageway 18, the area of which narrows with increasing height above a region of maximum cross-section at the level of a porous disc 20 disposed between the bases of two vertically aligned cones 22 and 24. The sparger 12 has an outlet 26 at its upper extremity and a venous inlet 28 at its lowest extremity. The sparger 12 also has an oxygen inlet 30 in communication with the passageway 18 at the region of maximum cross-section thereof at the level of the disc 20.

The oxygenation chamber 14 defines a serpentine cascade formed by a plurality of downwardly inclined ramps 32, 34 and 36. The oxygenation chamber 14 is coupled at its upper extremity to the sparger outlet 26. The oxygenation chamber 14 has an outlet 38 at its lowest extremity. The reservoir 16 is located beneath the outlet 38 of the oxygenation chamber 14 and has a concave foam filter 40 that defines a defoaming chamber 42 located directed below the outlet 38 of the oxygenation chamber 14. A heat exchanger 44 is at least partially located within the defoaming chamber 42. An arterial outlet 46 is located exteriorly of the reservoir 16.

The sparger 12 has a right cylindrical housing 48, preferably constructed of some transparent material, such as lucite. For ease of construction the sparger housing 48 may be a bifurcated structure, separable along a horizontal plane, although for clarity of illustration it is illustrated as a unitary structure. Within the sparger housing 48 a cavity is defined within which the two right circular cones 22 and 24 are located. The cones 22 and 24 must be impervious to fluid and constructed of a non-porous material, such as polycarbonate or lucite plastic. The conical surfaces of the cones 22 and 24 are inclined at an angle of about 30° relative to the vertical. The base of the inverted cone 24 is hollowed out to form an oxygen reservoir 50 at the center of and just beneath the porous disc 20. The oxygen inlet 30 is a plastic tube directed into the inverted cone 24 to empty into the oxygen reservoir 50 to thereby communicate with the porous disc 20.

The porous disc 20 is preferably constructed of sintered glass, and is preferably about 2⅛ inches in diameter and approximately ¼ inch thick. The solid, fluid impervious vertically aligned cones 22 and 24 are positioned base to base, the cone 22 being upright and the cone 24 being inverted. The porous disc 20 is interposed between the bases of the cones 22 and 24 in a sealed, fluid-tight relationship. Preferably, a fluid impervious adhesive is used to join the bases of the cones 22 and 24 to the circular faces of the disc 20. Care must be taken so that adhesive does not ooze onto the peripheral edge 21 of the disc 20, as this will produce non-uniformity in the emanation of gas containing oxygen into the passageway 18.

The cones 22 and 24 with the disc 20 therebetween are held in a vertically aligned upright disposition, as indicated in FIG. 2, by periodically spaced centering posts 52. The centering posts 52 extend outwardly from the interior surface defining the cavity within the housing 48 preferably a distance of three thirty-seconds of an inch. The centering posts 52 thereby maintain the interior housing surface and the external surfaces of the cones 22 and 24 and the disc 20 a distance of three thirty-seconds of an inch apart. The uniform spacing between these surfaces defines the width of the blood passageway 18.

As is evident from FIG. 2, the passageway 18 is of uniform width throughout and has a cross-sectional area that diminishes with distance both above and below the porous disc 20. The passageway 18 terminates at the sparger outlet 26 at the upper extremity of the housing 48. A venous inlet 28 at the bottom of the housing 48 leads to the passageway 18. Blood introduced as a liquid into the venous inlet 28 is transformed into a foam in the passageway adjacent the peripheral edge 21 of the porous disc 20 where a gas containing oxygen contacts the blood as it rises in the passageway 18 in liquid form. The gas enters the housing 48 through the oxygen inlet tube 30 and emanates radially from the peripheral edge 21 of the porous disc 20. From adjacent the porous disc 20, the liquid blood is transformed to a foam which rises upwardly in the passageway 18 between the interior surface of the housing 48 and the exterior of the surface of the cone 22 and is carried to the sparger outlet 26.

At the venous inlet 28 there is a downwardly angled Y-shaped cardiotomy connection 54 by means of which infusions of blood may be introduced into the blood oxygenator 10.

It is important for the cross-sectional area of the sparger outlet 26 to be at least as great as the cross-sectional area of the venous inlet 28. The venous inlet 28 is a standard ½ inch connection and the cardiotomy inlet 54 is a ⅜ths inch inlet. The oxygen tube 30 is a ¼ inch inlet. The sparger 12 also includes a radial thermometer pocket 56 defined in the housing 48 within which a temperature sensor can be placed to sense the temperature of the whole blood as it rises toward the sparger outlet 26.

A unique feature of the sparger 12 is that the blood passageway 18 is just large enough to offer minimal resistance to blood flow and, at the same time, to constrict gas bubble size and thereby force the gas and blood to mix. The uniform distribution of gas bubbles throughout the entire 360° perimeter of the peripheral edge 21 converts all of the blood to foam as the gas is radially introduced to mix with the blood. This creates a foam having a generally uniform bubble size. The blood passageway 18 is designed to be approximately the same size as the gas bubbles produced by the porous disc 20. Thus, gas and blood must occupy the same space and the amount of gas which is transferred to the blood is enhanced through the uniform and complete blood foam production.

The sparger design takes advantage of the natural tendency of a bubble to rise in a straight line when released into a liquid. By directing the blood up the inclined face of the cone 22 at an angle of approximately 30°, and by relying upon the gas tendency to rise straight upward, mixing of the gas and blood is enhanced. When the gas and blood, in a foam state, converge at the apex of the cone 22, all of the blood has been converted to a foam state. Thereafter, the foam is directed from the sparger outlet 26 to the oxygenation chamber 14 to allow oxygenation to occur and to allow the elimination of carbon dioxide from the blood foam to be completed.

The flow of blood foam through the serpentine cascade of the blood oxygenation chamber 14 occurs as indicated by the directional arrows. The ramps 32, 34 and 36 are inclined at an angle of from about 2° to about 5°. This construction provides for a protracted time of residency of the blood in contact with the oxygen and in a foam state, but allows an adequate flow rate.

From the outlet 38 of the oxygenation chamber 14, the blood flows into the reservoir 16. The reservoir 16 includes a transparent plastic casing 39 which houses the foam filter 40 and the heat exchanger 44. At the upper extremity of the reservoir 16 there is a flow guide 58 which is located between the upper extremities of the heat exchanger 44 and the oxygenation chamber outlet 38. The flow guide 58 is formed of a downwardly curved shield 60 which terminates at its upper extremity in a narrow ring 62 that is secured to the outlet 38. Within the shield 60 the flow guide 58 has a tent-shaped deflector 64, best illustrated in FIG. 3, which guides the downward flowing blood foam to either side of the upright loops 66 of the heat exchanger 44 therebeneath, which are visible in FIG. 4. The blood foam flows downwardly through slots 68 defined on opposite sides of the tent-shaped flow deflector 64. The blood foam flows downwardly onto the upper extremities of the upright loops 66 of the heat exchanger 44, traveling downwardly on the surface of the heat exchanger loops 66. The tent-shaped deflector 64 is connected to the shield 60 on opposite sides thereof at its corners, as depicted in FIG. 4, and the slots 68 are formed interiorally of the corner attachments. The shield 60 prevents blood from splashing outside of the defoaming chamber 42. The shield 60 extends downwardly well below the upper edge of the cup-shaped foam filter 40 to direct the flow of blood into the defoaming chamber 42.

The loops 66 of the heat exchanger 44 are aluminum coils, preferably ½ inch in diameter. Water is the heat exchange fluid which is circulated through the loops 66. The coils of the heat exchanger 44 are formed into elongated upright loops 66 that extend from the bottom of the defoaming chamber 42 to above the height of the foam filter 40, as best depicted in FIGS. 2 and 3. The heat exchanger 44 has laterally extending inlet and outlet connections 70 and 72. The flow guide 58 extends between the upper extremities of the upright loops 66 and the outlet 38 of the oxygenation chamber 14 to direct the flow of blood from the oxygenation chamber 14 onto the upper extremities of the heat exchanger loops 66 and into the defoaming chamber 42. The blood passes in rivulets and sheets down the surfaces of the aluminum loops 66. Because of the elongated design of the loops 66, the loops extend into the arterialized pool of blood in the reservoir 16 to allow control of the temperature of the blood so that it is maintained at body temperature in the reservoir 16 from which it is returned to the patient. The blood can either be heated or cooled as necessary.

An alternative heat exchanger construction is depicted in FIG. 7. In FIG. 7 a heat exchanger 44' is formed by helical coils 74 arranged to extend spirally upwardly about a vertical axis, along which a heat exchange fluid supply line 75 extends. The lowermost coils 74 positioned at the bottom of the defoaming chamber 42 and which encircle the axial supply line 75 are disposed at a greater distance and a larger diameter relative to the axial supply line 75, as compared with the uppermost of the helical coils 74. This design maximizes the volume of heat exchange tubing in contact with the blood, since the lowermost coils 74 are continuously in contact with the blood, while the uppermost coils 74 will sometimes be in contact with the blood, and sometimes not, depending upon the level of blood in the reservoir 16. In the embodiment of FIG. 7, the outer surface of the coils 74 is longitudinally corrugated or fluted, as illustrated in FIG. 8. This construction maximizes the heat transfer through the aluminum tubing of which the coils 74 are constructed.

The foam filter 40 is a conventional, standard silicone-"A" coated reticulated polyurethane defoaming sponge. The foam filter 40 is supported within an upright open cylindrical framework 76, best illustrated in FIG. 1. The framework 76 is a plastic, support framework with longitudinal supporting elements 78 and transverse, circular supporting elements 80. The purpose of the supporting framework 76 is to provide interior support for the foam filter 40 and to provide external support for the bubble screen 82 located thereabout. The supporting framework 76 terminates at its upper extremity in a circular support ring 84, which is held at periodic intervals by triangular struts 86 that maintain the supporting framework 76 at the center of the reservoir 16.

The screen 82 is a polyester screen of a measured and uniform pore or mesh size, preferably about 100 microns absolute. The screen 82 is carried upon the supporting framework 76 and surrounds the foam filter 40 to prevent undissolved gas in blood within the defoaming chamber 42 from passing outwardly toward the reservoir casing 39 to the arterial outlet 46. The screen 82 thereby serves as a "bubble point" barrier to prevent microgaseous emboli from being entrained in blood which is pumped to a patient. Bubble point is a physical phenomenon by means of which gas may not pass through a screen having a tight mesh size when the spaces in the mesh of the screen are wet. The appropriate mesh size to achieve this condition varies with the surface tensions of different materials and solutions in contact with the screen. Preferably, the mesh size of the polyester screen 82 in the present invention is no greater than about 150 microns absolute. This mesh size is ideal for preventing the passage of gaseous emboli in whole blood.

Because the ultimate limitation to blood flow is in the area of the final filter screen 82, it may be desirable for the polyurethane defoaming sponge to be of graded pore size in which the size of the pores increases with increasing distance from the screen 82. That is, it may be desirable for the pore size of the foam filter 40 to be greatest proximate to the coils 66 of the heat exhanger 44 and smallest proximate to the supporting framework 76 and the filter screen 82.

The floor 77 of the supporting structure 76 is constructed of solid plastic and slopes at a 2° to 5° incline toward the center where there is a drainage aperature 81. The supporting framework 76, with the polyester screen 82 thereabout, rests within an annular rim 90 on top of a transverse baffle plate 92, depicted in FIG. 6. The annular rim 90 laterally stabilizes the lower portion of the supporting framework 76 and keeps it centered within the reservoir 16. The baffle plate 92 is a disc constructed of plastic and has a cruciform opening at the center thereof, indicated at 94 in FIG. 6. The baffle plate 92 has upright supporting legs which are formed by two inverted bell-shaped flow directing partitions 96 and 98. The partitions 96 and 98 are slotted at their centers to interlock and are centered directly above the arterial outlet 46.

Beneath the floor of the reservoir casing 39 there is a central, axial cylindrical depending shell 100 within which a structure for inhibiting vortexing is positioned. The vortexing inhibiting structure is indicated at 102 in FIG. 2 and includes an upright body having a solid top 104 and walls with lateral openings therein indicated at 106. The vortex inhibiting structure 102 is disposed in the shell 100 in the arterial outlet 46 below the level of the reservoir 16.

Together, the vortex inhibiting structure 106, the baffle plate 92 and the partitions 96 and 98 tend to arrest circular motion in a liquid draining through the arterial outlet 46 for a distance of at least 5 inches thereabove. Accordingly, any vortex formed is quite shallow, and air does not become entrained therein. The means provided for inhibiting vortexing prevents air bubbles from being entrapped at the arterial outlet 46, so that potential emboli are not passed to a patient as blood from the reservoir 16 is returned to the patient.

Figure 1:
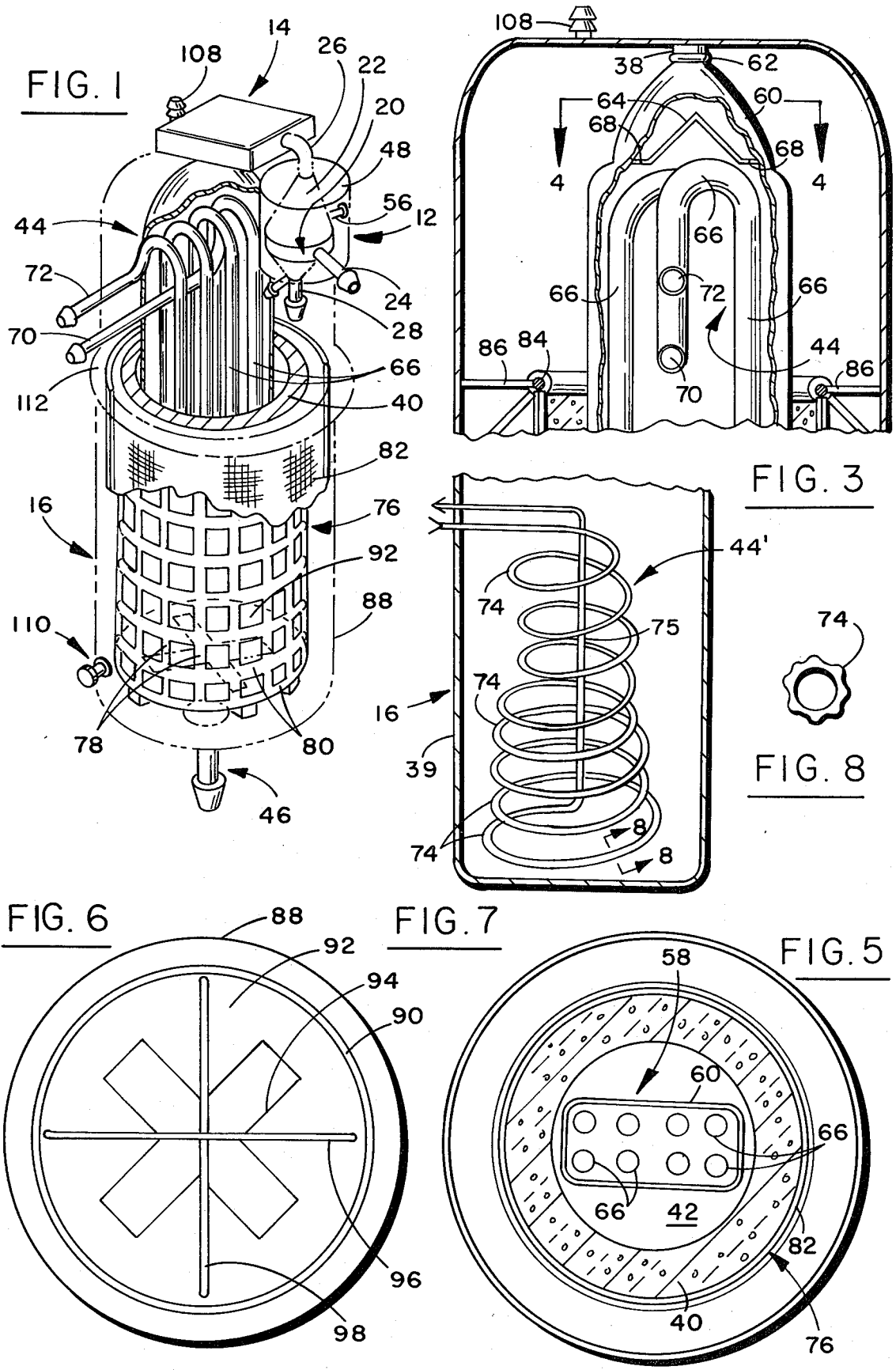
FIG. 1 is a perspective view showing the blood oxygenator of the invention with portions partially broken away.

The preferred form of the invention also includes other features which are typical of conventional prior art devices. For example, and as illustrated in FIGS. 1–3, a rapid priming port nipple or luer 108 projects upwardly from the top of the reservoir casing 16. A priming solution, blood and medication can be added rapidly to the reservoir 16 by means of the nipple 108 at the rapid priming port. The nipple 108 is a standard ¼ inch fitting.

A temperature probe nipple is also provided near the bottom of the reservoir 16 and is indicated at 110 in FIGS. 1 and 2. The temperature probe nipple is capped off in the embodiment as illustrated, but a thermometer or other temperature sensor could be inserted to extend into shielded thermal contact with the arterialized blood in the lower portion of the casing 39 of the reservoir 16. In this way the blood temperature an be accurately monitored to ensure that the arterialized blood is returned to the patient at body temperature. Any temperature adjustments can be performed by increasing or decreasing the temperature or flow rate of the water circulating through the heat exchanger 44.

The casing 39 is preferably formed of two parts which fit together with a frictional fit at a vent 112. The vent 112 includes a bonnet at the lower extremity of the upper portion of the casing 39 and extends in an arc of about 180° around the circumference of the casing 39. A gap between the casing portions allows gases to escape from the reservoir 16 in the space between the casing sections at the vent 112.

In the operation of the invention, venous blood from a patient is introduced into the venous inlet 28 of the sparger 12 while gas containing oxygen is directed into the gas inlet 30. Foaming of the blood is effectuated adjacent the periphery of the disc 20 in the sparger 12 and the blood foam rises in the annular sparger passageway to the sparger outlet 26. The blood foam then passes to the oxygenation chamber 14, where is cascades down the inclined ramps 32, 34 and 36. In the oxygenation chamber oxygen is dissolved in the blood and carbon dioxide is driven out of the blood so that the blood leaves the oxygenation chamber enriched in oxygen, or "arterialized". At the oxygenation chamber outlet 38 the blood foam flows into the reservoir 16, confined by the shield 60 and falling onto the flow deflector 64 of the flow guide 58. The blood foam falls through the slots 68 onto the upper portions of the heat exchanger coil loops 66. The blood flows down the loops 66 and into the defoaming chamber 42. The blood then passes radially outwardly through the foam filter 40. The filter 40 transforms the blood and allows it to pass outwardly therethrough only as a liquid. Entrained gas in the liquid, arterialized blood is blocked by the screen 82, so that all blood reaching the arterial outlet 46 has been liquified and freed of entrained bubbles. The arterialized blood flows to the arterial outlet 46. The baffle plate 92, the partitions 96 and 98, and the vortex inhibiting structure 102 all aid in preventing the formation of a vortex and the consequent entrainment of gas in the blood as it flows back to the arterial system of the patient. The blood oxygenator 10 is disposed of following use.

Undoubtedly numerous modifications and variations of the invention will become readily apparent to those familiar with blood oxygenators. For example, the arterial outlet 46 could be moved from the center of the floor of the casing 39 of the reservoir 16 to the edge for improved visibility to a perfusionist. Other variations and modifications are also contemplated for use in blood oxygenators constructed according to the invention.

Accordingly, the scope of the invention should not be construed as limited to the specific embodiments of the invention depicted, but rather the invention is defined in the claims appended hereto.

We claim:

1. In a sparger for a blood oxygenator which defines a passageway, a venous inlet at the lower extremity of said passageway, an outlet at the upper extremity of said passageway, and an oxygen inlet means, the improvement wherein said passageway is annular and of uniform width and has fluid impervious walls, and the width of said passageway is between about one thirty-second and three-eighths of an inch, and the cross sectional area of said passageway narrows with increasing height above a region of maximum cross section to said outlet, and said oxygen inlet means has a porous, radial, disc-edge periphery in communication with said passageway at said region of maximum cross section.

2. A blood oxygenator according to claim 1 in which said sparger passageway is about three thirty-seconds of an inch in width.

3. A blood oxygenator according to claim 2 in which the cross-sectional area of said sparger outlet is at least one-half of one square inch.

4. A blood oxygenator according to claim 1 in which said sparger has an interior surface shaped as the surfaces of two right circular cones positioned base to base with a porous disc defining said porous radial disc-edge periphery interposed therebetween.

5. A blood oxygenator according to claim 4 in which said sparger passageway has surfaces inclined at an angle of about 30° relative to the vertical.

6. A blood oxygenator according to claim 4 in which said sparger is formed by a housing defining a cavity therewithin, and further comprising a pair of solid, fluid impervious vertically aligned cones positioned base to base, one upright and one inverted, with said porous disc interposed in fluid-tight relationship therebetween, and said oxygen inlet includes a tube directed into the inverted one of said cones and into communication with said porous disc, whereby oxygen is introduced into blood in said passageway radially from the periphery of said porous disc.

7. An improved blood oxygenator according to claim 6 wherein said passageway is further defined between said inverted cone and said housing and is of a cross-sectional area that diminishes with distance below said disc and terminates at said venous inlet, and said oxygen tube extends into said inverted cone to communicate with said disc.

8. A sparger according to claim 6 further comprising spacing means projecting from one of said housing and said inverted cone to contact the other thereof to thereby maintain said passageway at a uniform width throughout.

* * * * *